United States Patent [19]

Shiomura et al.

[11] Patent Number: 4,937,339
[45] Date of Patent: Jun. 26, 1990

[54] PROCESS FOR PREPARING ISOCYANURATE RING-CONTAINING MATERIALS

[75] Inventors: Tetsunosuke Shiomura, Tokyo; Yoshiho Sonobe, Yokohama; Akihiro Yamaguchi, Kamakura; Ryuzi Haseyama, Yokohama, all of Japan

[73] Assignee: Mitsui Toatsu Chemicals, Incorporated, Tokyo, Japan

[21] Appl. No.: 295,201

[22] PCT Filed: May 18, 1988

[86] PCT No.: PCT/JP88/00470
§ 371 Date: Dec. 16, 1988
§ 102(e) Date: Dec. 16, 1988

[87] PCT Pub. No.: WO88/09329
PCT Pub. Date: Dec. 1, 1988

[30] Foreign Application Priority Data

May 20, 1987 [JP] Japan ................................. 62-121042
May 21, 1987 [JP] Japan ................................. 62-122605

[51] Int. Cl.⁵ ........................................... C07D 251/32
[52] U.S. Cl. ..................................................... 544/193
[58] Field of Search .......................................... 544/193

[56] References Cited

U.S. PATENT DOCUMENTS

| 3,609,149 | 9/1971 | Matsui et al. | 260/248 |
| 4,487,928 | 12/1984 | Richter et al. | 544/193 |
| 4,865,795 | 9/1989 | Shiomura et al. | 528/57 |

FOREIGN PATENT DOCUMENTS

| 46-15298 | 2/1971 | Japan | 544/193 |
| 46-31531 | 6/1971 | Japan | 544/193 |

OTHER PUBLICATIONS

Saunders, J. H., and K. C. Frisch, "Polyurethanes: Chemistry and Technology" (1962), p. 24.

Primary Examiner—Richard A. Schwartz
Assistant Examiner—J. Richter
Attorney, Agent, or Firm—Fisher, Christen & Sabol

[57] ABSTRACT

In a process for preparing isocyanurate ring-containing materials useful in the production of lacquers and foams which comprises trimerizing an organic isocyanate compound in the presence of a catalyst, the use of potassium fluoride as the catalyst makes it possible to yield the desired product rapidly without formation of by-products. More preferably, the reaction efficiency can further be enhanced by using a polyethylene oxide compound, a quaternary ammonium salt and/or a phosphonium compound in combination with potassium fluoride.

22 Claims, No Drawings

PROCESS FOR PREPARING ISOCYANURATE RING-CONTAINING MATERIALS

DESCRIPTION

TECHNICAL FIELD

This invention relates to a novel process for preparing isocyanurate ring-containing materials which are useful in the production of lacquers and foams.

BACKGROUND ART

Isocyanurate ring-containing materials are usually prepared by trimerizing an organic isocyanate compound in the presence of a catalyst. Catalysts suitable for the trimerization include organic strong bases such as alkali metal salts of carboxylic acids, alkali metal phenolates, alkali metal carbonates, tertiary amines, tertiary phosphines, onium compounds of nitrogen or phosphorus, and as well as heterocyclic compounds containing such elements [see J. H. Saunders and K. C. Frisch, "Polyurethanes: Chemistry and Technology" (1962), p. 94]. Moreover, it is known that the reaction products of Mannich bases or tertiary amines with alkyl esters of phosphoric acid, phosphorous acid or phosphoric acid can also be used as trimerization catalysts.

However, such conventional trimerization catalysts have the disadvantage that they tend to yield yellow-colored reaction products. Another disadvantage thereof is that, where 2,4-tolylene diisocyanate is used as the starting material, it is very difficult to yield its trimer selectively without careful control of reaction conditions such as the amount of catalyst, reaction temperature and reaction time. Consequently, polynuclear by-products having poor solubility tend to be formed.

The object of the present invention is to overcome the above described disadvantages of the prior art processes for preparing the trimers of organic isocyanate compounds by using conventional catalysts.

As a result of extensive investigation of the reactions of isocyanates, the present inventor has found that potassium fluoride catalytically accelerates the trimerization of organic isocyanate compounds. The present invention has been completed on the basis of this finding.

DISCLOSURE OF INVENTION

According to the present invention, there is provided a process for preparing isocyanurate ring-containing materials by trimerization of an organic isocyanate compound, the process being characterized in that potassium fluoride is used as the catalyst, preferably in combination with a polyethylene oxide compound, a quaternary ammonium salt and/or a phosphonium compound.

BEST MODE FOR CARRYING OUT THE INVENTION

The potassium fluoride used in the process of the present invention can take any of various forms including pellets, powder and flakes. However, it is preferable from the viewpoint of catalytic activity and economy to use potassium fluoride in powder form. The potassium fluoride can be supported on a carrier such as celite or active carbon.

The process of the present invention can be applied to organic isocyanate compounds such as aliphatic and aromatic mono-, di- or polyisocyanates. Preferred examples of aliphatic isocyanates include methyl isocyanate, n-butyl isocyanate, n-octyl isocyanate, stearyl isocyanate, hexamethylene diisocyanate and isophorone diisocyanate, and preferred examples of aromatic isocyanate include phenyl isocyanate, 2,4- and 2,6-tolylene diisocyanates, and diphenylmethane diisocyanate. Where diisocyanates (such as 2,4-tolylene diisocyanate) having two isocyanate groups different in reactivity from each other are used, there can readily be prepared isocyanurate ring-containing polyisocyanates in which only half of the starting isocyanate groups have participated in the reaction.

Moreover, where one or more certain compounds known as phase transfer catalysts are used in combination with potassium fluoride, the rate of trimerization of the organic isocyanate compound can be markedly enhanced as compared with that achievable with potassium fluoride alone.

More specifically, such certain compounds comprise one or more compounds selected from the groups consisting of (i) polyethylene oxide compounds, (ii) quaternary ammonium salts and (iii) phosphonium compounds.

Examples of the compounds falling within the aforesaid categories of (i) to (iii) are as follows.

Useful polyethylene oxide compounds (i) include, for example, ethylene glycol dimethyl ether, diethylene glycol dimethyl ether and polyethylene glycols such as polyethylene glycol, polyethylene glycol monomethyl ether and polyethylene glycol dimethyl ether; crown ethers such as dibenzo-18-crown-6, dicyclohexyl-18-crown-6- and 18-crown-6-other; and cryptands such as $C_{14}H_{28}N_2O_4$ and $C_{16}H_{32}N_2O_5$, more specifically 4,7,13,18-tetraoxa-1,10-diaza bicyclo[8. 5. 5]eicosane:

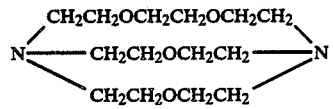

and 4,7,13,16,21-pentaoxa-1,10-diazabicyclo[8. 8. 5]tricosane:

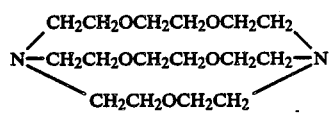

which are commercially produced by Merck Co., available from Kanto Chemicals Co. under the trademarks KRYPTOFIX-211 and KRYPTOFIX-221, respectively. Useful quaternary ammonium salts (ii) include, for example, tris(dioxa-3,6-heptyl)amine, benzyltriethylammonium chloride and tetrabutylammonium bromide. Useful phosphonium compounds (iii) include, for example, trioctylethylphosphonium bromide, tetraphenylphosphonium chloride and tetrabutylphosphonium chloride.

Among the aforesaid compounds (i) to (iii), polyethylene oxide compounds (i) are especially preferred because they are highly effective in accelerating the reaction.

Potassium fluoride, which serves as the catalyst, is preferably used in an amount of 0.0001 to 0.05 part by weight, more preferably 0.001 to 0.05 part by weight, per part by weight of the organic isocyanate compound used. One or more of the aforesaid compounds (i) to (iii) are preferably used in an amount of 1/100 to 100 times, more preferably 1/10 to 5 times, the amount of potassium fluoride.

The trimerization reaction is carried out in the presence or absence of a solvent inert to isocyanates. The solvents used in the process of the present invention can be selected from organic solvents commonly used in the reactions of isocyanates. Preferred examples of such solvents include esters such as ethyl acetate and butyl acetate; ketones such as acetone and methyl ethyl ketone; aromatic substances such as benzene, toluene and xylene; and aprotic solvents such as dimethyl sulfoxide, tetramethyl sulfone, tetrahydrofuran, N-methylpyrrolidone, N,N-dimethylformamide, N,N'-tetramethylurea and 1,3-dimethylimidazolidinone.

The characteristic feature of the present invention is that potassium fluoride is used as the catalyst. It is to be understood that sodium fluoride or lithium chloride is utterly ineffective.

Where a solvent is used, the reaction is carried out by dissolving the organic isocyanate compound in the solvent, dispersing therein potassium fluoride, either alone or together with one or more of the compounds (i) to (iii), and then maintaining the resultant reaction mixture at a temperature ranging from room temperature to about 150° C. The reaction time can range from 0.1 to 40 hours when potassium fluoride is used alone, and can range from 1 second to several hours when one or more of the compounds (i) to (iii) are additionally used. Since potassium fluoride is scarcely soluble in the aforesaid organic solvents (0.1 g/l or less), it can be easily recovered by filtering the reaction mixture after completion of the reaction. After filtration, the desired trimer can be easily separated and recovered from the solvent according to conventional techniques such as concentration and cooling.

Where no solvent is used, the reaction can be carried out by dispersing potassium fluoride directly in the organic isocyanate compound and then heating the resultant reaction mixture. Where one or more of the compounds (i) to (iii) are additionally used, it is preferable to dissolve them in a portion of the organic isocyanate compound and add the resultant solution to the remainder thereof.

Since potassium fluoride loses its catalytic activity in the presence of water, it is essential to carry out the reaction under anhydrous conditions. Moreover, since the aforesaid reaction is suppressed in the presence of air, the reaction is preferably carried out in a vacuum or an inert atmosphere.

The present process for preparing the trimers of organic isocyanate compounds has the following advantages, as compared with the prior art processes.

(1) Since side reactions hardly occur, the raw material efficiency is high and, moreover, the resultant trimer can be separated and purified with great ease. Especially when 2,4-tolylene diisocyanate is used as the starting material, only its trimer is yielded without formation of polynuclear by-products. Thus, the resultant product has good solubility in solvents and is suitable for use in coating compositions.

(2) Since the resultant trimer is nearly colorless and transparent, it provides high product value.

(3) Since the presence of residual potassium fluoride catalyst has no adverse effect on the quality of the products, it is possible in many cases to omit the separation and purification steps.

(4) Great economy is achieved because the catalyst is used in very small amounts and potassium fluoride is commercially available at low cost.

Moreover, where one or more of the compounds (i) to (iii) are used in combination with potassium fluoride, the following additional advantages are obtained.

(5) The reaction rate is very high and the yield reaches approximately 100%.

(6) When 2,4-tolylene diisocyanate is used as the starting material, the trimer in which only the 4-isocyanate groups have reacted is obtained quantitatively. Even if the reaction temperature is elevated or the reaction time is prolonged, the 2-isocyanate groups do not undergo autocondensation any longer. Thus, no polynuclear by-products are formed and the resultant product has good solubility in solvents.

(7) The process of the present invention makes it possible to prepare liquid oligomers in which 5 to 70 percent of the isocyanate groups present in polyvalent isocyanate monomers such as 2,4-tolylene diisocyanate and diphenylmethane diisocyanate have reacted so as to form isocyanurate rings. The liquid oligomers so prepared can be reacted with polyols to form polyurethanes containing isocyanurate linkages. These polyurethanes are useful as foams and elastomers.

The present invention is further illustrated by the following examples. In all cases, the reaction was carried out in an inert atmosphere obtained by replacement with nitrogen.

EXAMPLE 1

A 300-ml three neck flask was charged with 50 g of n-butyl isocyanate, 100 ml of xylene and 2 g of potassium fluoride which had been vacuum-dried at 150° C. for 3 hours. This reaction mixture was heated at 120° C. for 8 hours. After it was cooled to room temperature, potassium fluoride was filtered off to obtain a clear solution. After the xylene and, any unreacted n-butyl isocyanate were removed by distillation under reduced pressure, 3 g of the distillate having a boiling range of 130-150° C. at 2 mmHg was obtained. The results of its elemental analysis were as follows: C, 61.0% (calcd. 60.6%); H, 9.3% (calcd. 9.1%); N, 13.9% (calcd. 14.1%). Thus, the found values were in good agreement with the values calculated for the cyclic trimer. The infrared spectrum of the product exhibited a strong absorption band at 1680 $cm^{-1}$ which was characteristic of the isocyanurate group, and did not exhibit any absorption band at 2280 $cm^{-1}$ due to unreacted isocyanate groups.

EXAMPLE 2

A reaction vessel was charged with 50 g of 2,4-tolylene diisocyanate, 100 ml of butyl acetate and 0.5 g of potassium fluoride which had been vacuum-dried at 150° C. for 3 hours. After this reaction mixture was heated at 120° C. for 3 hours, the suspended potassium fluoride was removed by filtration. Then, the reaction mixture was heated under a vacuum of 2 mmHg to remove the solvent and thereby a white solid weighing 11 g was obtained. The results of its elemental analysis were as follows: C, 61.6% (calcd. 62.1%); H, 3.4% (calcd. 3.4%); N, 16.0% (calcd. 16.1%). Thus, the found values were in good agreement with the values calculated for the cyclic trimer. When the product was analyzed by the dibutylamine method, its NCO content was found to be 24.8%. This value was very close to the theoretical value for the cyclic trimer (i.e., 24.1%).

For purposes of comparison, a commercially available 2,4-tolylene diisocyanate trimer (Colonate 2030; manufactured by Nippon Polyurethane Industries Ltd.) was freed of solvent and then vacuum-dried in a stream of nitrogen. This commercial product showed no definite melting point up to 300° C., whereas the product of the above example showed a melting point of 130–135° C. The vacuum-dried commercial product had an NCO content of 15.0%.

EXAMPLE 3

40 mg of potassium fluoride and 40 mg of tris(dioxa-3,6-heptyl)amine (TDA-1; manufactured by Rhone-Poulenc Inc.) were added to 40 g of 2,4-tolylene diisocyanate. This reaction mixture was warmed to 50° C. After 3 minutes, the reaction mixture became highly viscous and could not be stirred no longer. After 5 minutes, it solidified to form a white mass. After cooling, the mass was crushed, washed three times with 200 cc portions of hexane, and then vacuum-dried at room temperature. The yield was almost quantitative. The found values of elemental analysis of the reaction product were as follows: C, 62.1%; H, 3.4%; N, 16.1%. Its infrared absorption spectrum exhibited an —NCO absorption band at 2250 cm$^{-1}$ and a —C=O absorption band at 1700 cm$^{-1}$, both having almost identical intensities.

EXAMPLE 4

At room temperature, 100 mg of potassium fluoride and 50 mg of 18-crown-6-ether (manufactured by Tokyo Kasei K.K.) were added to 40 g of 2,4-tolylene diisocyanate. Immediately after the addition of the crown compound, the reaction mixture solidified to form a white mass. When the product was dissolved in butyl acetate and analyzed by the di-n-butylamine method, its NCO content was found to be 24.8%. This value was very close to that calculated for the trimer (i.e., 24.1%).

EXAMPLE 5

5 ml of n-butyl isocyanate, 50 ml of N-methylpyrrolidone, 0.2 g of potassium fluoride and 0.1 g of trimethyl-benzylammonium chloride were mixed. This reaction mixture was heated at 120° C. for 4 hours and then poured into 300 cc of water. The oily layer was separated and extracted three times with water to remove the solvent, or N-methylpyrrolidone. Thereafter, the oily layer was vacuum-dried to obtain 2.2 g of product. The results of its elemental analysis were as follows: C, 60.4% (calcd. 60.6%); H, 9.4% (calcd. 9.1%); N, 13.8% (calcd. 14.1%). These found values were in good agreement with the values calculated for the cyclic trimer.

EXAMPLE 6

50 g of diphenylmethane diisocyanate, 0.5 g of potassium fluoride and 0.5 g of butylsulfonium chloride were added to 100 ml of butyl acetate. This reaction mixture was heated at 120° C. for 3 hours and then filtered to remove the suspended potassium fluoride. Thereafter, the solvent was distilled off under reduced pressure to obtain a white solid weighing 48 g. When this product was analyzed by the dibutylamine method, its NCO content was found to be 13.4%. Thus, the degree of isocyanurate ring formation was 58%.

COMPARATIVE EXAMPLE 1

Reaction was carried out in the same manner as described in Example 2, except that 0.5 g of sodium fluoride was used in place of potassium fluoride. After the completion of the reaction, the catalyst was filtered off and the reaction mixture was distilled at 2 mmHg. When temperature was gradually raised to 200° C., there was essentially no residue.

We claim:

1. Process for preparing isocyanurate ring-containing material by the trimerization of an organic isocyanate compound, the process being characterized in that potassium fluoride is used as the catalyst, the potassium fluoride is present in a catalytic effective amount, the catalytic trimerization is conducted under anhydrous conditions, the process is conducted in the absence of air, the catalytic trimerization is conducted at a temperature effective for conducting the catalytic trimerization, and the process is conducted at a pressure effective for conducting the catalytic trimerization.

2. The process as claimed in claim 1 wherein the potassium fluoride is used in an amount of 0.0001 to 0.05 part by weight per part by weight of the organic isocyanate compound.

3. The process as claimed in claim 1 wherein the potassium fluoride is used in an amount of 0.001 to 0.05 part by weight per part by weight of the organic isocyanate compound.

4. The process as claimed in claim 1 wherein the catalytic trimerization is conducted in a vacuum or in an inert atmosphere.

5. The process as claimed in claim 1 wherein the temperature is from room temperature to about 150° C.

6. The process as claimed in claim 1 wherein the catalytic trimerization is conducted in an organic solvent which is inert to isocyanates.

7. The process as claimed in claim 6 wherein the organic solvent is an ester, a ketone, an aromatic substance or an aprotic solvent.

8. The process as claimed in claim 6 wherein the organic solvent is ethyl acetate, butyl acetate, acetone, methyl ethyl ketone, benzene, toluene, xylene, dimethyl sulfoxide, tetramethyl sulfone, tetrahydrofuran, N-methylpyrrolidone, N,N-dimethylformamide, N,N'-tetramethylurea or 1,3-dimethylimidazolidinone.

9. The process as claimed in claim 1 wherein the potassium fluoride in the form of pellets, powder or flakes.

10. The process as claimed in claim 1 wherein the potassium fluoride is in powder form.

11. The process as claimed in claim 1 wherein the potassium fluoride is supported on an inert carrier.

12. The process as claimed in claim 1 wherein the organic isocyanate compound is an aliphatic monoisocyanate, an aliphatic diisocyante, an aliphatic polyisocyanate, an aromatic monoisocyanate, an aromatic diisocyanate or an aromatic polyisocyanate.

13. The process as claimed in claim 1 wherein the organic isocyanate compound is methyl isocyanate, n-butyl isocyanate, n-octyl isocyanate, stearyl isocyanate, hexamethylene diisocyanate or isophorone diisocyanate.

14. The process as claimed in claim 1 wherein the organic isocyanate compound is phenyl isocyanate, 2,4-tolylene diisocyanate, 2,6-tolylene diisocyanate or diphenylmethane diisocyanate.

15. The process as claimed in claim 1 wherein the organic isocyanate compound is an organic diisocyanate compound having two isocyanate groups which are different in reactivity from each other.

16. The process as claimed in claim 1 wherein one or more compounds selected from the group consisting of (i) polyethylene oxide compounds, (ii) quaternary ammonium salts and (iii) phosphine compounds, is used in combination with potassium fluoride.

17. The process as claimed in claim 16 wherein a polyethylene oxide compound is used in combination with potassium fluoride.

18. The process as claimed in claim 16 wherein the polyethylene oxide compound is ethylene glycol dimethyl ether, diethylene glycol, dimethyl ether, polyethylene glycol, polyethylene glycol monomethyl ether, polyethylene glycol dimethyl ether, dibenzo-18-crown-6-ether, dicyclohexyl-18-crown-6-ether, 18-crown-6-ether, cryptand $C_{14}H_{28}N_2O_4$ and cryptand $C_{16}H_3N_2O_5$.

19. The process as claimed in claim 16 wherein the quaternary ammonium salt is tris(dioxa-3,6-heptyl)amine, benzyltriethylammonium chloride or tetrabutylammonium bromide.

20. The process as claimed in claim 16 wherein the phosphonium compound is trioctylethylphosphonium bromide, tetraphenylphosphonium chloride or tetrabutylphosphonium chloride.

21. The process as claimed in claim 16 wherein the one or more compounds selected from the group consisting of (i) to (iii) are used in an amount of 1/100 to 100 times that of potassium fluoride.

22. The process as claimed in claim 16 wherein the one or more compounds selected from the group consisting of (i) to (iii) are used in an amount of 1/10 to 5 times that of potassium fluoride.

* * * * *